United States Patent [19]

Kurauchi et al.

[11] Patent Number: 5,565,575

[45] Date of Patent: Oct. 15, 1996

[54] METHOD FOR THE PRODUCTION OF 5-CYCLOHEXYLMETHYLHYDANTOIN DERIVATIVES

[75] Inventors: Masahiko Kurauchi; Kunisuke Izawa, both of Kawasaki, Japan

[73] Assignee: Ajinomoto Co., Inc., Tokyo, Japan

[21] Appl. No.: 440,841

[22] Filed: May 15, 1995

Related U.S. Application Data

[63] Continuation of Ser. No. 177,321, Jan. 4, 1994, abandoned.

[30] Foreign Application Priority Data

Jan. 4, 1993 [JP] Japan ..................... 5-000089

[51] Int. Cl.[6] ................................. C07D 233/96
[52] U.S. Cl. ..................... 548/317.1; 548/319.1; 548/320.1; 548/320.5; 548/321.1
[58] Field of Search ............ 548/317.1, 321.1, 548/319.1, 320.1, 320.5

[56] References Cited

U.S. PATENT DOCUMENTS

| 2,861,079 | 11/1958 | Britton et al. | 548/321.1 |
| 4,582,903 | 4/1986 | Mirviss | 544/139 |
| 4,684,736 | 8/1987 | Mirviss | 548/308 |

*Primary Examiner*—Jacqueline Haley
*Attorney, Agent, or Firm*—Oblon, Spivak, McClelland, Maier & Neustadt, P.C.

[57] ABSTRACT

5-Cyclohexylmethylhydantoin derivatives may be conveniently prepared by reducing, in the presence of a metal catalyst, a 5-(3-cyclohexene-1-yl)melthylenehydantoin derivative which is obtained by the condensation of a hydantoin derivative and a 3-cyclohexene-1-carbaldehyde derivative in the presence of a monoalkanolamine.

21 Claims, No Drawings

METHOD FOR THE PRODUCTION OF 5-CYCLOHEXYLMETHYLHYDANTOIN DERIVATIVES

This is a continuation of application Ser. No. 08/177,321 filed on Jan. 4, 1994 now abandoned.

BACKGROUND OF THE INVENTION

1. Field of the Invention

The present invention relates to a method for the production of 5-cyclohexylmethylhydantoin derivatives which are useful as starting materials for the production of drugs, and to 5-(3-cyclohexene-1-yl)methylenehydantoin derivatives which are intermediates for the production of such 5-cyclohexylmethylhydantoin derivatives.

2. Discussion of the Background

2-Amino-3-cyclohexylpropionic acid (β-cyclohexylalanine) is a compound whose importance as a constituent of drugs has been increasing in recent years (J. R. Luly, et al., *J. Med. Chem.*, vol. 31, p.2264 (1988)). Many methods for the synthesis of β-cyclohexylalanine are known, and one of the potent synthetic methods is a method involving the hydrolysis of 5-cyclohexylmethylhydantoin (A. Kleemann, et al., Japanese Patent Application Disclosure SHO 57-150645; Kaneko, et al., *Amino Acid Industry*, 5-7 Kodansha, 1973).

5-Cyclohexylmethylhydantoin may be obtained by the reduction of 5-cyclohexylmethylenehydantoin, and the methods which are known for the production of 5-cyclohexylmethylenehydantoin include (A) a method in which 5-cyclohexylmethylenehydantoin is obtained by the reaction of phosphonyl hydantoin obtained by the bromination of hydantoin at the 5-position followed by phosphonation thereof by a Michaelis-Arbuzov reaction, with cyclohexane carbaldehyde (N. A. Meanwell, et al., *J. Org. Chem.*, vol. 56, p.6897 (1991)), and is then reduced; and (B) a method in which cyclohexane carbaldehyde is condensed directly with hydantoin. However, there are problems with Method (A), because it involves many steps, and also because cyclohexane carbaldehyde is costly. In addition, Method (B) has the same disadvantage of using the costly cyclohexane carbaldehyde, and therefore neither method can be said to be industrially useful.

Thus, there remains a need for a simple, safe, and low-cost method for the production of 5-cyclohexylmethylhydantoin and derivatives thereof. There also remains a need for intermediates useful in such a method for the production of 5-cyclohexylmethylhydantoin and derivatives thereof.

SUMMARY OF THE INVENTION

Accordingly, it is one object of the present invention to provide a simple, safe and low-cost novel method for the production of 5-cyclohexylmethylhydantoin and derivatives thereof.

It is another object of the present invention to provide novel intermediates useful for the production 5-cyclohexylmethylhydantoin and derivatives thereof.

It is another object of the present invention to provide a novel method for the production of such intermediates.

These and other objects, which will become apparent during the following detailed description, have been achieved by the inventors' discovery that two of the carbon-carbon double bonds of 5-(3-cyclohexene-1-yl)methylenehydantoin derivatives, which may be easily synthesized by the condensation of a hydantoin derivative and a 3-cyclohexene-1-carbaldehyde derivative, are easily reduced in the presence of a metal catalyst to yield a 5-cyclohexylmethylhydantoin derivative.

In other words, the present invention provides 5-(3-cyclohexene-1-yl)methylenehydantoin derivatives represented by the following general formula (I)

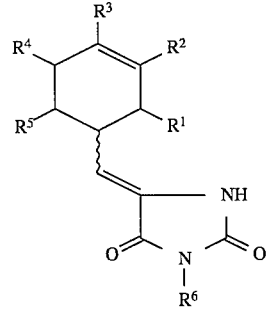

wherein $R^1$, $R^2$, $R^3$, $R^4$, and $R^5$ each independently represent hydrogen, a substituted or unsubstituted alkyl group, substituted or unsubstituted cycloalkyl group, substituted or unsubstituted aryl group, substituted or unsubstituted alkoxy group, or substituted or unsubstituted cycloalkoxy group; and $R^6$ represents hydrogen, a substituted or unsubstituted alkyl group, or substituted or unsubstituted aryl group, as well as a method for the production of a 5-cyclohexylmethylhydantoin derivative represented by the general formula (IV) below, which comprises reducing, in the presence of a metal catalyst, a 5-(3-cyclohexene-1-yl)-methylenehydantoin derivative represented by the general formula (I) below. The present invention also provides a method for preparing the 5-(3-cyclohexene-1-yl)-methylenehydantoin derivative of general formula (I) below by the condensation of a hydantoin derivative represented by the general formula (II) below and a 3-cyclohexene-1-carbaldehyde derivative represented by the general formula (III) below in the presence of a monoalkanolamine;

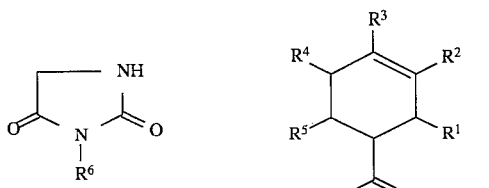

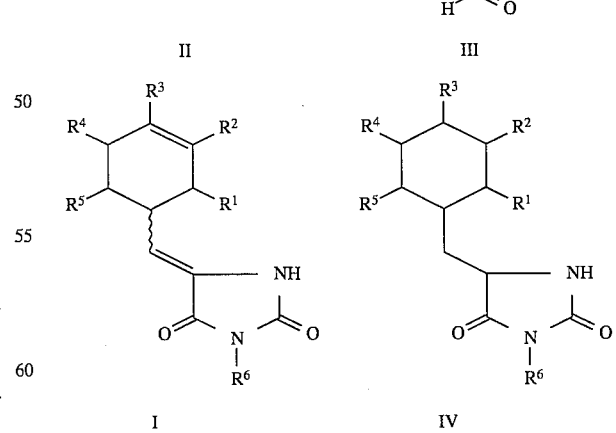

wherein $R^1$, $R^2$, $R^3$, $R^4$, and $R^5$ each independently represent hydrogen, a substituted or unsubstituted alkyl group, substituted or unsubstituted cycloalkyl group, substituted or unsubstituted aryl group, substituted or unsubstituted alkoxy group, or substituted or unsubstituted cycloalkoxy group; and $R^6$ represents hydrogen, a substituted or unsubstituted alkyl group, or substituted or unsubstituted aryl group.

DETAILED DESCRIPTION OF THE PREFERRED EMBODIMENTS $R^1$, $R^2$, $R^3$, $R^4$, and $R^5$ in the 5-(-cyclohexene-1-yl)-methylenehydantoin derivative represented by the general formula (I), the 3-cyclohexene-1-carbaldehyde derivative represented by the general formula (III) and the 5-cyclohexylmethylhydantoin derivative represented by the general formula (IV) may each be, for example, hydrogen; an alkyl group of 1–20 carbon atoms which may be unsubstituted or substituted with one or more groups selected from the group consisting of $C_{6-10}$-aryl (phenyl, tolyl, naphthyl, etc.), amino, $C_{1-4}$-alkylamino, di($C_{1-4}$-alkyl)amino, $C_{1-4}$-alkoxy, hydroxy, and halogen, for example, the substituted or unsubstituted alkyl group may be a methyl, ethyl, propyl, isopropyl, butyl, sec-butyl, tert-butyl, n-hexyl, n-octyl, n-octadecyl, benzyl, phenethyl, naphthylmethyl, aminomethyl or methoxymethyl group, etc.; a cycloalkyl group of 5–8 carbon atoms, such as cyclopentyl, cyclohexyl, cycloheptyl or cyclooctyl; an aryl group of 6–20 carbon atoms which may be unsubstituted or substituted with one or more groups selected from the group consisting of hydroxy, $C_{1-4}$-alkoxy,, amino, $C_{1-4}$-alkylamino, di($C_{1-4}$-alkyl)amino, $C_{1-4}$-alkyl, and halogen, for example, the unsubstituted or substituted aryl group may be a phenyl, hydroxyphenyl, methoxyphenyl, aminophenyl, tolyl, xylyl, cumenyl, naphthyl, anthryl or fluorenyl group, etc.; an alkoxy group of 1–20 carbon atoms which may be unsubstituted or substituted with one or more $C_{6-10}$-aryl groups (e.g., phenyl, naphthyl, etc.), for example, the unsubstituted or substituted alkoxy group may be a methoxy, ethoxy, propyloxy, isopropyloxy, butyloxy, sec-butyloxy, tert-butyloxy, n-hexyloxy, n-octyloxy, n-octadecyloxy or benzyloxy group, etc.; or a cycloalkoxy group of 5 to 8 carbon atoms, such as cyclopentyloxy, cyclohexyloxy, cycloheptyloxy, and cyclooctyloxy; and they are not particularly restricted thereto. In addition, examples of $R^6$ in the 5-(-cyclohexene-1-yl)methylenehydantoin derivatives represented by the general formula (I), the hydantoin derivatives represented by the general formula (II) and the 5-cyclohexylmethylhydantoin derivatives represented by the general formula (IV) may be, for example, hydrogen; an alkyl group of 1–7 carbon atoms which may be unsubstituted or substituted with one or more $C_{6-10}$-aryl groups (e.g., phenyl, naphthyl, etc.), for example, the unsubstituted or substituted alkyl group may be a methyl, ethyl, propyl, isopropyl or benzyl group, etc.; or an aryl group of 6–10 carbon atoms which may be unsubstituted or substituted with one or more $C_{1-4}$-alkyl groups, for example, the unsubstituted or substituted aryl group may be a phenyl, tolyl or naphthyl group, etc.; and it is not particularly restricted thereto.

The compounds of formula (I), (III), and (IV) contain a number of asymmetrically substituted carbon atoms. Thus, the carbon atoms to which $R^1$, $R^4$, and $R^5$ are attached, as well as the carbon atom to which the carbaldehyde group in formula (III) is attached, are all asymmetrically substituted and capable of existing in one of two possible configurations. The compounds of formulae (I), (III), and (IV) include all possible stereoisomers, including mixtures of diastereomers and enantiomers, as well as purified diastereomers and enantioners. In addition, the wavey line connecting the cyclohexenyl ring to the carbon-carbon double bond in formula (I) indicates that the compounds of formula (I) include those in which the carbon-carbon double bond has either the E or Z configuration as well as mixtures of compounds having E and Z configurations.

The 5-(3-cyclohexene-1-yl)methylenehydantoin derivatives according to the present invention may be produced by the condensation of a hydantoin derivative of formula (II) and a 3-cyclohexene-1-carbaldehyde derivative of formula (III), which is easily and economically produced by a Diels-Alder reaction between an acrolein derivative and a butadiene derivative, in the presence of a monoalkanolamine. The 3-cyclohexene-1-carbaldehyde derivative of formula (III) in which each of $R^1$, $R^2$, $R^3$, $R^4$, and $R^5$ is hydrogen (1,2,3,6-tetrahydrobenzaldehyde) is a commercially available compound. As an example of a method for the condensation of a hydantoin and an aldehyde in the presence of a monoalkanolamine, there is the known method of E. C. Britton, et al. described in U.S. Pat. No. 2,861,079, which is incorporated herein by reference, but no instance exists of this method being applied to the substances according to the present invention.

The mole ratio of the 3-cyclohexene-1-carbaldehyde derivative of formula (III) and the hydantoin derivative of formula (II) in the condensation reaction for the production of the 5-(3-cyclohexene-1-yl)methylenehydantoin derivative of formula (I) is 0.8:1 to 1.5:1, and preferably 1:1 to 1.3:1.

The solvent to be used for the above mentioned condensation reaction is not particularly restricted so long as it does not itself react, exerts no adverse effect on the reaction, and is capable of dissolving the starting materials to the degree which is necessary for the reaction, and examples of suitable solvents include water, methanol, ethanol, propanol, isopropanol, ethylene glycol, dimethylformamide, dimethylacetamide, N-methylpyrrolidone, N,N'-dimethylimidazolidinone, tetrahydrofuran, dioxane, ethyleneglycol monomethyl ether, ethyleneglycol dimethyl ether, etc., or mixtures of these solvents. The amount of these solvents to be used is not particularly limited so long as it is sufficient to allow efficient stirring of the reaction solution, but normally the weight of the solvent is 1 to 20 times, and preferably 2 to 10 times, with respect to the weight of the hydantoin derivative of formula (II).

Furthermore, the monoalkanolamine to be used in the above mentioned condensation reaction is not particularly restricted so long as it is capable of smoothly promoting the reaction, and examples thereof include ethanolamine, propanolamine, butanolamine, and the like. The amount of monoalkanolamine to be used is not particularly restricted so long as it is sufficient to allow completion of the desired reaction, but it is normally 10 to 90 mole percent, and preferably 30 to 70 mole percent, with respect to the number of moles of the hydantoin derivative of formula (II).

For the condensation, the hydantoin derivative of formula (II), the 3-cyclohexene-1-carbaldehyde derivative of formula (III), the monoalkanolamine and the solvent may be added at one time to the reactor, and then heated and stirred until the reaction goes to completion.

The reaction temperature for the condensation is not particularly restricted so long as it is a temperature which promotes the reaction without decomposing the product, and there is normally no problem if it is of a level which allows a gentle reflux of the solution. For convenience, the condensation reaction may be carried out at a temperature of from room temperature (about 20° C.) to the boiling point of any of the above-mentioned solvents at atmospheric pressure.

The solvent to be used in the reduction reaction of the 5-(3-cyclohexene-1-yl)methylenehydantoin derivative of formula (I) to the 5-cyclohexylmethylhydantoin derivative of formula (IV) is not particularly restricted so long as it does not itself react, exerts no adverse effect on the reaction, and is capable of dissolving the starting materials to the degree which is necessary for the reaction, and examples of such solvents include water, aqueous caustic soda solution, methanol, ethanol, propanol, isopropanol, ethylene glycol, dimethylformamide, dimethylacetamide, N-methylpyrrolidone, N,N'-dimethylimidazolidinone, tetrahydrofuran, dioxane, ethyleneglycol monomethyl ether, ethyleneglycol dimethyl ether, acetic acid, propionic acid, or mixtures of these solvents, etc. The amount of these solvents to be used is not particularly restricted so long as it is sufficient to allow efficient stirring of the reaction solution, but normally the weight of the solvent is 2 to 20 times, and preferably 4 to 15 times, with respect to the weight of the 5-(3-cyclohexene-1-yl)methylenehydantoin derivative of formula (I).

The metal catalyst to be used for the reduction is not particularly restricted so long as it smoothly promotes the reaction, and for example, palladium, platinum, rhodium, nickel and the like may be mentioned. In addition, these may be carried on carbon or the like, or may contain water. The amount of the metal catalyst to be used is not particularly restricted so long as it is sufficient to allow completion of the desired reaction, but normally it is 0.01 to 10 mole percent, and preferably 0.1 to 5 mole percent, with respect to the number of moles of the 5-(3-cyclohexene-1-yl)methylenehydantoin derivative of formula (I).

The reduction reaction may be carried out by adding the 5-(3-cyclohexene-1-yl)methylenehydantoin derivative of formula (I), the metal catalyst, and the solvent to the reactor at one time, and then stirring the mixture under a hydrogen atmosphere to the completion of the reaction. The hydrogen pressure is not particularly limited so long as the reaction is smoothly promoted, but it is normally 1 to 300 kg/cm$^2$, and preferably 1 to 150 kg/cm$^2$.

The reaction temperature is not particularly restricted so long as it is a temperature which promotes the reaction without decomposing the product, but it is normally 0° to 150° C., and preferably 10° to 100° C.

The 5-(3-cyclohexene-1-yl)methylenehydantoin derivatives of formula (I) provided according to the present invention are compounds which may be produced very easily and economically. By using these compounds as starting materials, it has become possible to provide an excellent method for the production of the 5-cyclohexylmethylhydantoin derivatives of formula (IV), which are important compounds as intermediates for the synthesis of 2-amino-3-cyclohexylpropionic acid and derivatives thereof.

Other features of the invention will become apparent in the course of the following descriptions of exemplary embodiments which are given for illustration of the invention and are not intended to be limiting thereof.

EXAMPLES

Example 1

Synthesis of 5-(3-cyclohexene-1-yl)methylenehydantoin.

Fifty milliliters of water, 20 ml of isopropyl alcohol, 20.00 g of hydantoin, 24.22 g of 3-cyclohexene-1-carbaldehyde and 6.10 g of monoethanolamine were placed in a reactor equipped with a mechanical stirrer and a reflux condenser, the mixture was stirred in an oil bath at 120° C. while refluxing. After 3 hours of continued heating and stirring, the solution was cooled to 10° C., and the precipitated crystals were collected by filtration. These were suspended in 100 ml of a mixed solution of water and isopropyl alcohol (volumetric ratio=2:5), after which the crystals were again collected by filtration and dried under reduced pressure at 40° C. overnight, to obtain 33.45 g of 5-(3-cyclohexene-1-yl)methylenehydantoin. The yield was 87.0%. The crude crystals were recrystallized from ethanol to obtain a pure product.

Mass spectra analysis (FAB mode) Calculated: (M+H$^+$ $C_{10}H_{13}N_2O_2$): 193.0977 Found: 193.0979

Nuclear magnetic resonance analysis ($^1$H DMSO)

$\delta$1.43(1H, m), 1.64(1H, m), 1.86(1H, m), 2.04(2H, m), 2.10(1H, m), 2.81(1H, m), 5.44(1H, d), 5.66(2H, m), 10.17(1H, bs), 10.94(1H, bs)

Nuclear magnetic resonance analysis ($^{13}$C, DMSO)

$\delta$23.59, 27.41, 30.12, 30.85, 115.87, 125.36, 126.63, 129.31, 154.74, 164.54

Infrared spectroscopic analysis (KBr)

cm$^{-1}$ 3150, 3020, 1766, 1725, 1682, 1400, 1198, 1085, 855, 752

Thin-layer chromatography (ethyl acetate:n-hexane=4:1) Rf=0.69

Example 2

Synthesis of 5-cyclohexylmethylhydantoin

Forty milliliters of ethyleneglycol monomethyl ether, 3.84 g of 5-(3-cyclohexene-1-yl)methylenehydantoin and 0.43 g of wet 10% palladium on carbon (moisture 50%) were placed in a reactor equipped with a mechanical stirrer and a reflux condenser, and the mixture was reduced while stirring at 50° C. under a hydrogen pressure of 3 kg/cm$^2$. After 4 hours, the reaction mixture was heated to 90° C. and the resulting precipitate was dissolved, after which the palladium on carbon was removed by filtering the hot mixture. To the slurry obtained by concentrating the filtrate to about 20 ml was added 100 ml of water, by which were obtained white crystals which were then collected by filtration and washed with water, and then dried under reduced pressure at 60° C. overnight to obtain 3.50 g of 5-cyclohexylmethylhydantoin. The yield was 89.2%. The crude crystals were recrystallized from ethanol to obtain a pure product.

Mass spectrum analysis (FAB mode) Calculated: (M+H$^+$ $C_{10}H_{17}N_2O_2$): 197.1290 Found: 197.1302

Infrared spectroscopic analysis (KBr) cm$^{-1}$ 3223, 2361, 2029, 1767, 1732, 1425, 1258, 1196, 1121, 1013, 802, 461

Thin-layer chromatography (ethyl acetate:n-hexane=4:1) Rf=0.49

Example 3

Synthesis of 5-cyclohexylmethylhydantoin

Twenty-five milliliters of a 5% aqueous sodium hydroxide solution, 3.84 g of 5-(3-cyclohexene-1-yl)methylenehydantoin and 0.43 g of wet 10% palladium on carbon (moisture 50%) were placed in a reactor equipped with a mechanical stirrer and a reflux condenser, and the mixture was reduced while stirring at 45° C. under a hydrogen pressure of 3.5 kg/cm$^2$. After 9 hours, the palladium on carbon was removed by filtration, and the pH of the filtrate was adjusted to about 3 by addition of 1N hydrochloric acid, upon which white crystals were obtained. These were collected by filtration and washed with water, and then dried under reduced pressure at 60° C. overnight to obtain 3.43 g of 5-cyclohexylmethylhydantoin. The yield was 87.4%.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A method for the production of a 5-cyclohexylmethylhydantoin represented by formula IV:

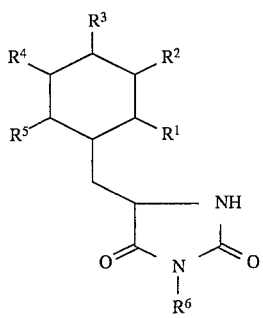

IV which comprises:
(i) condensing a hydantoin represented by the formula II and a 3-cyclohexene-1-carbaldehyde represented by the formula III in the presence of a monoalkanolamine

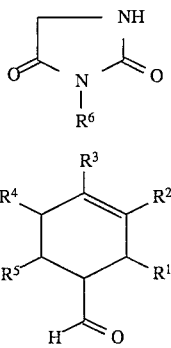

II

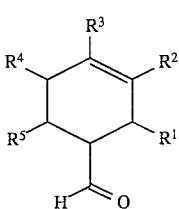

III to obtain a 5-(3-cyclohexene-1-yl)methylenehydantoin represented by formula (I)

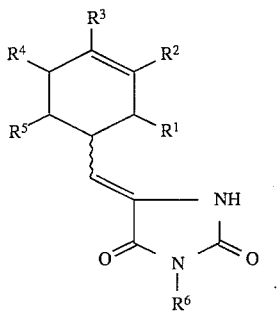

I and
(ii) reducing said 5-(3-cyclohexene-1-yl)-methylenehydantoin in the presence of a metal catalyst to obtain said 5-cyclohexylmethylhydantoin, wherein $R^1$, $R^2$, $R^3$, $R^4$, and $R^5$ each independently represent hydrogen, a substituted or unsubstituted alkyl group, substituted or unsubstituted cycloalkyl group, substituted or unsubstituted aryl group, substituted or unsubstituted alkoxy group, or substituted or unsubstituted cycloalkoxy group; and $R^6$ represents hydrogen, a substituted or unsubstituted alkyl group, or a substituted or unsubstituted aryl group.

2. The method of claim 1, wherein $R^1$, $R^2$, $R^3$, $R^4$, and $R^5$ each independently represent hydrogen; an alkyl group of 1–20 carbon atoms which may be substituted with one or more groups selected from the group consisting of $C_{6-10}$-aryl, amino, $C_{1-4}$-alkylamino, di($C_{1-4}$-alkyl)amino, $C_{1-4}$-alkoxy, hydroxy, and halogen; a cycloalkyl group of 5–8 carbon atoms; an aryl group of 6–20 carbon atoms which may be substituted with one or more groups selected from the group consisting of hydroxy, $C_{1-4}$-alkoxy, amino, $C_{1-4}$-alkylamino, di($C_{1-4}$-alkyl)amino, $C_{1-4}$-alkyl, and halogen; an alkoxy group of 1–20 carbon atoms which may be substituted with one or more $C_{6-10}$-aryl groups; or a cycloalkoxy group of 5 to 8 carbon atoms; and $R^6$ represents hydrogen; an alkyl group of 1–7 carbon atoms which may be substituted with one or more $C_{6-10}$-aryl groups; or an aryl group of 6–10 carbon atoms which may be substituted with one or more $C_{1-4}$-alkyl groups.

3. The method of claim 1, wherein $R^1$, $R^2$, $R^3$, $R^4$, and $R^5$ each independently are selected from the group consisting of hydrogen, methyl, ethyl, propyl, isopropyl, butyl, sec-butyl, tert-butyl, n-hexyl, n-octyl, n-octadecyl, benzyl, phenethyl, naphthylmethyl, aminomethyl, methoxymethyl, cyclopentyl, cyclohexyl, cycloheptyl, cyclooctyl, phenyl, hydroxyphenyl, methoxyphenyl, aminophenyl, tolyl, xylyl, cumenyl, naphthyl, anthryl, fluorenyl, methoxy, ethoxy, propyloxy, isopropyloxy, butyloxy, sec-butyloxy, tert-butyloxy, n-hexyloxy, n-octyloxy, n-octadecyloxy, benzyloxy, cyclopentyloxy, cyclohexyloxy, cycloheptyloxy, and cyclooctyloxy; and $R^6$ is selected from the group consisting of hydrogen, methyl, ethyl, propyl, isopropyl, benzyl, phenyl, tolyl, and naphthyl.

4. The method of claim 1, wherein said monalkanolamine is selected from the group consisting of ethanolamine, propanolamine, and butanolamine.

5. The method of claim 1, wherein said metal catalyst is selected from the group consisting of palladium, platinum, rhodium, and nickel.

6. The method of claim 1, wherein said condensing step (i) is conducted in the presence of an inert solvent which dissolves said hydantoin of the formula (II) and the 3-cyclohexene-1-carbaldehyde of the formula (III).

7. The method of claim 6, wherein said condensing step (i) is conducted at a temperature of from about ambient temperature to the boiling point of said inert solvent.

8. The method of claim 1, wherein said reducing step (ii) is conducted at a temperature from about 0° to 150° C.

9. The method of claim 8, wherein said reducing step (ii) is conducted at a temperature of from about 10° to 100° C.

10. A method for the production of a 5-(3-cyclohexene-1-yl)methylenehydantoin represented by the formula I

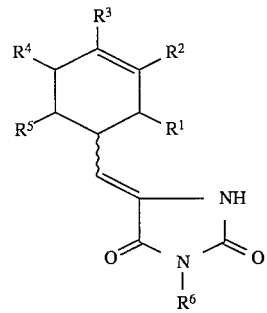

I which comprises condensing a hydantoin derivative represented by the formula II and a 3-cyclohexene-1- carbaldehyde represented by the formula III below in the presence of a monoalkanolamine

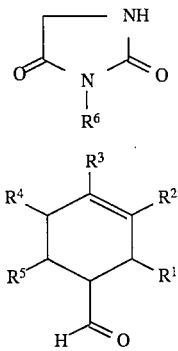

wherein $R^1$, $R^2$, $R^3$, $R^4$, and $R^5$ each independently represent hydrogen, a substituted or unsubstituted alkyl group, a substituted or unsubstituted cyclalkyl group, substituted or unsubstituted aryl group, substituted or unsubstituted alkoxy group, or a substituted or unsubstituted cycloalkoxy group; and $R^6$ represents hydrogen, a substituted or unsubstituted alkyl group, or a substituted or unsubstituted aryl group.

11. The method of claim 10, wherein $R^1$, $R^2$, $R^3$, $R^4$, and $R^5$ each independently represent hydrogen; an alkyl group of 1–20 carbon atoms which may be substituted with one or more groups selected from the group consisting of $C_{6-10}$-aryl, amino, $C_{1-4}$-alkylamino, di($C_{1-4}$-alkyl)amino, $C_{1-4}$-alkoxy, hydroxy, and halogen; a cycloalkyl group of 5–8 carbon atoms; an aryl group of 6–20 carbon atoms which may be substituted with one or more groups selected from the group consisting of hydroxy, $C_{1-4}$-alkoxy, amino, $C_{1-4}$-alkylamino, di($C_{1-4}$-alkyl)amino, $C_{1-4}$-alkyl, and halogen; an alkoxy group of 1–20 carbon atoms which may be substituted with one or more $C_{6-10}$-aryl groups; or a cycloalkoxy group of 5 to 8 carbon atoms; and $R^6$ represents hydrogen; an alkyl group of 1–7 carbon atoms which may be substituted with one or more $C_{6-10}$-aryl groups; or an aryl group of 6–10 carbon atoms which may be substituted with one or more $C_{1-4}$-alkyl groups.

12. The method of claim 10, wherein $R^1$, $R^2$, $R^3$, $R^4$, and $R^5$ each independently are selected from the group consisting of hydrogen, methyl, ethyl, propyl, isopropyl, butyl, sec-butyl, tert-butyl, n-hexyl, n-octyl, n-octadecyl, benzyl, phenethyl, naphthylmethyl, aminomethyl, methoxymethyl, cyclopentyl, cyclohexyl, cycloheptyl, cyclooctyl, phenyl, hydroxyphenyl, methoxyphenyl, aminophenyl, tolyl, xylyl, cumenyl, naphthyl, anthryl, fluorenyl, methoxy, ethoxy, propyloxy, isopropyloxy, butyloxy, sec-butyloxy, tert-butyloxy, n-hexyloxy, n-octyloxy, n-octadecyloxy, benzyloxy, cyclopentyloxy, cyclohexyloxy, cycloheptyloxy, and cyclooctyloxy; and R6 is selected from the group consisting of hydrogen, methyl, ethyl, propyl, isopropyl, benzyl, phenyl, tolyl, and naphthyl.

13. The method of claim 10, wherein said monalkanolamine is selected from the group consisting of ethanolamine, propanolamine, and butanolamine.

14. The method of claim 10, wherein said condensing step is conducted in the presence of an inert solvent which dissolves said hydantoin of the formula (II) and the 3-cyclohexene-1-carbaldehyde of the formula (III).

15. The method of claim 10, wherein said condensing step is conducted at a temperature of from ambient temperature to the boiling point of said solvent.

16. A method for the production of a 5-cyclohexylmethylhydantoin represented by the formula IV

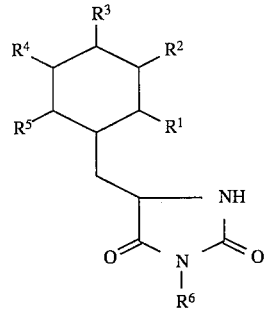

which comprises reducing a 5-(3-cyclohexene-1-yl)-methylenehydantoin represented by the formula I below, in the presence of a metal catalyst

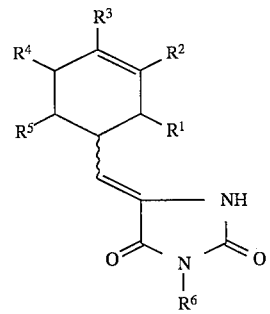

wherein $R^1$, $R^2$, $R^3$, $R^4$, and $R^5$ each independently represent hydrogen, a substituted or unsubstituted alkyl group, substituted or unsubstituted cycloalkyl group, substituted or unsubstituted aryl group, substituted or unsubstituted alkoxy group, or substituted or unsubstituted cycloalkoxy group; and $R^6$ represents hydrogen, a substituted or unsubstituted alkyl group, or a substituted or unsubstituted aryl group.

17. The method of claim 16, wherein $R^1$, $R^2$, $R^3$, $R^4$, and $R^5$ each independently represent hydrogen; an alkyl group of 1–20 carbon atoms which may be substituted with one or more groups selected from the group consisting of $C_{6-10}$-aryl, amino, $C_{1-4}$-alkylamino, di($C_{1-4}$-alkyl)amino, C1-4-alkoxy, hydroxy, and halogen; a cycloalkyl group of 5–8 carbon atoms; an aryl group of 6–20 carbon atoms which may be substituted with one or more groups selected from the group consisting of hydroxy, $C_{1-4}$-alkoxy, amino, $C_{1-4}$-alkylamino, di($C_{1-4}$-alkyl)amino, $C_{1-4}$-alkyl, and halogen; an alkoxy group of 1–20 carbon atoms which may be substituted with one or more $C_{6-10}$-aryl groups; or a cycloalkoxy group of 5 to 8 carbon atoms; and $R^6$ represents hydrogen; an alkyl group of 1–7 carbon atoms which may be substituted with one or more $C_{6-10}$-aryl groups; or an aryl group of 6–10 carbon atoms which may be substituted with one or more $C_{1-4}$-alkyl groups.

18. The method of claim 16, wherein $R^1$, $R^2$, $R^3$, $R^4$, and $R^5$ each independently are selected from the group consisting of hydrogen, methyl, ethyl, propyl, isopropyl, butyl, sec-butyl, tert-butyl, n-hexyl, n-octyl, n-octadecyl, benzyl, phenethyl, naphthylmethyl, aminomethyl, methoxymethyl, cyclopentyl, cyclohexyl, cycloheptyl, cyclooctyl, phenyl, hydroxyphenyl, methoxyphenyl, aminophenyl, tolyl, xylyl, cumenyl, naphthyl, anthryl, fluorenyl, methoxy, ethoxy, propyloxy, isopropyloxy, butyloxy, sec-butyloxy, tert-butyloxy, n-hexyloxy, n-octyloxy, n-octadecyloxy, benzyloxy, cyclopentyloxY, cyclohexyloxy, cycloheptyloxy, and cyclooctyloxy; and $R^6$ is selected from the group consisting of hydrogen, methyl, ethyl, propyl, isopropyl, benzyl, phenyl, tolyl, and naphthyl.

19. The method of claim 16, wherein said metal catalyst is selected from the group consisting of palladium, platinum, rhodium, and nickel.

20. The method of claim 16, wherein said reducing step is conducted at a temperature from 0° to 150° C.

21. The method of claim 20, wherein said reducing step is conducted at a temperature of from 10° to 100° C.

* * * * *